(12) United States Patent
Weil et al.

(10) Patent No.: US 6,413,497 B1
(45) Date of Patent: Jul. 2, 2002

(54) PHARMACEUTICAL COMPOSITION USING A MIXTURE OF PROPELLANT GASES FOR A METERED DOSE INHALER

(75) Inventors: Hans-Hermann Weil, Gau-Bickelheim; Ottfried Daab, Ingelheim, both of (DE)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/566,105

(22) Filed: May 5, 2000

Related U.S. Application Data

(63) Continuation of application No. 08/659,812, filed on Jun. 7, 1996, now abandoned.

(30) Foreign Application Priority Data

Feb. 3, 1990 (DE) .......................................... 40 03 272

(51) Int. Cl.⁷ ................................................ A61K 9/12
(52) U.S. Cl. .......................................... 424/45; 424/46
(58) Field of Search ..................................... 424/45, 46

(56) References Cited

U.S. PATENT DOCUMENTS 4,174,295 A * 11/1979 Bargigia et al.
4,352,789 A     10/1982 Thiel
4,405,598 A      9/1983 Brown
4,814,161 A      3/1989 Jinks et al.
5,118,494 A *    6/1992 Schultz et al.
5,190,029 A *    3/1993 Byron et al.
5,225,183 A *    7/1993 Purewal et al.
5,776,432 A *    7/1998 Schultz et al.
6,004,537 A *   12/1999 Blondino et al.
6,013,245 A *    1/2000 Taylor et al.
6,039,932 A *    3/2000 Govind et al.

FOREIGN PATENT DOCUMENTS

| EP | 0 341 559 A2 | 11/1989 |
| GB | 902590 | 8/1962 |
| GB | 1 525 181 | 9/1978 |
| WO | 86/04233 A1 | 7/1986 |
| WO | 88/01165 A1 | 2/1988 |

* cited by examiner

*Primary Examiner*—Raj Bawa
(74) *Attorney, Agent, or Firm*—Robert P. Raymond; Mary-Ellen M. Devlin; Alan R. Stempel

(57) ABSTRACT

New advantageous propellant gas mixtures contain two or more components, at least one of which is a partially fluorinated lower alkane, and may be used in pharmaceutical preparations.

6 Claims, No Drawings

PHARMACEUTICAL COMPOSITION USING A MIXTURE OF PROPELLANT GASES FOR A METERED DOSE INHALER

This is a continuation of Ser. No. 08/659,812 filed Jun. 7, 1996, now abandoned.

The invention relates to new propellent gas mixtures which contain as a typical ingredient partially fluorinated lower alkanes such as 1,1,1,2,3,3,3-heptafluoropropane (TG 227), the use of these propellent gas mixtures in pharmaceutical preparations suitable for the production of aerosols, and these pharmaceutical preparations themselves.

Aerosols of powdered (micronised) drugs are used widely in therapy, e.g. in the treatment of obstructive diseases of the respiratory tract. If such aerosols are not produced by atomising the pharmaceutical powder or by spraying solutions, suspensions of the drugs in liquefied propellent gases are used. The latter consist primarily of mixtures of TG 11 (trichlorofluoromethane), TG 12 (dichlorodifluoromethane) and TG 114 (1,2-dichloro-1,1,2, 2-tetrafluoroethane), optionally with the addition of lower alkanes such as butane or pentane, or with the addition of DME (dimethylether). Mixtures of this kind are known for example from German Patent 1178975.

owing to their harmful effect on the earth's atmosphere (destruction of the ozone layer, Greenhouse effect) the use of chlorofluorocarbons has become a problem, with the result that the search is on for other propellent gases or propellent gas mixtures which do not have the above-mentioned harmful effects or, at least, have them to a lesser degree.

However, this search has come up against major problems, since propellent gases for therapeutic use have to satisfy numerous criteria which cannot easily be reconciled, e.g. in terms of toxicity, stability, vapour pressure, density and solubility characteristics.

As has now been found, propellent gas mixtures consisting of two or more components and containing at least one partially fluorinated lower alkane and optionally one or more compounds of the group TG 11, TG 12, TG 114, lower alkane and dimethylether, are particularly suitable for use in therapeutical preparations.

Partially fluorinated lower alkanes which are particularly suitable for the purposes of the invention are TG 227 (1,1,1,2,3,3,3-heptafluoropropane), TG 125 (pentafluoroethane), TG 134a (1,1,1, 2-tetrafluoroethane) and TG 152a (1,1-difluoroethane). Of the alkanes, propane, butane and pentane, preferably the n-compounds, are particularly suitable. To optimise the properties of the propellent gas mixture it may be useful to add amounts of the propellent gases TG 11, TG 12 and TG 114, which are the ones most frequently used hitherto, as they have a relatively high density. Pharmaceutical preparations produced on the basis of the new propellent gas mixtures generally contain in addition to the active substance (e.g. in suspended form) a surface-active substance conventionally used for this purpose, e.g. an ester of a polyalcohol, perhaps a sorbitan ester with higher saturated or unsaturated fatty acids, e.g. sorbitan trioleate, or a polyethoxysorbitan ester of a higher, preferably unsaturated fatty acid or a phospholipid, possibly a lecithin. The adjuvant may be present in the mixture either dissolved or undissolved.

In order to inhibit the sedimenting of suspended particles of drug, it is advisable to use mixtures of liquefied propellent gases having a density which does not differ substantially from the density of the suspended substance. However, it is also possible to use mixtures with greater differences in density between the pharmaceutical substance and the liquefied propellent gas mixture. In fact, it has been found that suspensions which separate out can easily be uniformly distributed again in the suspension medium proposed here simply by shaking.

The ratios of quantities of the individual ingredients of the propellent gas mixture may be varied within wide limits. The proportions (in percent by weight are 10 to 99% for TG 227, 20 to 75% for TG 125, 20 to 75% for TG 134a and 25 to 80% for 152a. The mixture may also contain 0 to 50% propane and/or butane and/or pentane and/or DME and 0 to 25% TG 11, TG 12 and/or TG 114. Within the limits specified, the ingredients are selected to add up to 100%. Propellent gas mixtures containing 30 to 95% of TG 227 are preferred.

The proportion of suspended drug in the finished preparation is between 0.001 and 5%, preferably between 0.005 and 3%, more particularly between 0.01 and 2%. The surface-active substances are added in amounts of from 0.01 to 10%, preferably 0.05 to 5%, more particularly 0.1 to 3% (here, as in the case of the pharmaceutical substances, the percentage by weight of the finished preparation is given). The pharmaceutical substances used in the new preparations may be any of the substances suitable for use by inhalation or possibly for intranasal administration. They include, therefore, in particular betamimetics, anticholinergics, steroids, antiallergics, PAF-antagonists and combinations of these active substances.

The following are given as specific examples:

Examples of Betamimetics:

Bambuterol
Bitolterol
Carbuterol
Clenbuterol
Fenoterol
Hexoprenalin
Ibuterol
Pirbuterol
Procaterol
Reproterol
Salbutamol
Salmeterol
Sulfonterol
Terbutalin
Tulobuterol
1-(2-fluoro-4-hydroxyphenyl)-2-[4-(1-benzimnidazolyl)-2-methyl-2-butylamino]ethanol
erythro-5'-hydroxy-8'-(1-hydroxy-2-isopropylaminobutyl)-2H-1,4-benzoxazin-3-(4H)-one
1-(4-amino-3-chloro-5-trifluoromethylphenyl)-2-tert.-butylamino) ethanol
1-(4-ethoxycarbonylamino-3-cyano-5-fluorophenyl)-2-(tert.-butylamino) ethanol.

Examples of Anticholinergics:

Ipratropium bromide
Oxitropium bromide
Trospium chloride
Benzilic acid-N-β-fluoroethylnortropine ester methobromide Examples of Steroids:

Budesonide
Beclomethasone (or the 17, 21-dipropionate thereof)

Dexamethason-21-isonicotinate
Flunisolide

Examples of Antiallergics:
Disodium cromoglycate
Nedocromil

Examples of PAF-antagonists:
WEB 2086
WEB 2170
WEB 2347

The active substances may also be combined, e.g. betamimetics plus anticholinergics or betamimetics plus antiallergics.

Examples of preparations according to the invention (amounts given in percent by weight):

| | | | | | |
|---|---|---|---|---|---|
| 1) | 0.10% | Oxitropium bromide | 2) | 0.3% | Fenoterol |
| | 0.01% | Soya lecithin | | 0.1% | Soya lecithin |
| | 4.0% | Pentane | | 10.0% | Pentane |
| | 95.89% | TG 227 | | 70.0% | TG 227 |
| | | | | 19.6% | TG 134a |
| 3) | 0.1% | Ipratropium bromide | 4) | 0.3% | Fenoterol |
| | 0.1% | Soya lecithin | | 0.1% | Soya lecithin |
| | 25.0% | Pentane | | 30.0% | TG 11 |
| | 10.1% | TG 227 | | 49.6% | TG 134a |
| | 64.7% | TG 134a | | 20.0% | TG 227 |
| 5) | 1.5% | Disodium cromoglicate | 6) | 0.3% | Salbutamol |
| | | | | 0.2% | Span 85 |
| | 0.1% | Tween 20 | | 20.0% | Pentane |
| | 97.0% | TG 227 | | 30.0% | TG 227 |
| | 1.4% | Butane | | 49.5% | TG 134a |
| 7) | 0.15% | Fenoterol | 8) | 0.1% | Ipratropium-bromide |
| | 0.06% | Ipratropium-bromide | | 0.1% | Soya lecithin |
| | 0.10% | Soya lecithin | | 20.3% | TG 125 |
| | 40.00% | TG 11 | | 25.5% | TG 152a |
| | 39.69% | TG 134a | | 54.0% | TG 227 |
| | 20.00% | TG 227 | | | |

What is claimed is:

1. A pharmaceutical composition of matter suitable for inhalation comprising a pharmaceutically active compound or substance in an amount of about 0.00% to about 5% by weight and a liquted gas mixture of 1,1,1,2,3,3,3-heptafluorouropane in an amount of 30 to 95% by weight and one or more alkanes selected from the group consisting of 1,1,1,2-tetrafluoroethane in an amount of 20–75% by weight, pentafluoroethane in an amount of 20–75% by weight, trichlorofluoromethane in an amount of 0–25% by weight and 1,2-dichloro-1,1,2,2-tetrafluoroethane in an amount of 0–25% by weight.

2. The pharmaceutical composition of matter as recited in claim 1 comprising 1,1,1,2-tetrafluoroethane.

3. The pharmaceutical composition of matter as recited in claim 1 further comprising a surface-active substance in an amount from about 0.01% to about 10% by weight of the composition.

4. The pharmaceutical composition of matter as recited in claim 3 wherein the surface-active substance is a phospholipid, a sorbitan ester with a higher saturated or unsaturated fatty acid or a polyethoxy sorbitan ester of a higher fatty acid.

5. The pharmaceutical composition of matter as recited in claim 3 wherein the surface-active substance is a lecithin, a polyoxyethylene sorbitan oleate or a sorbitan trioleate.

6. The pharmaceutical composition of matter as recited in claim 1 wherein the pharmaceutically active compound or substance is a betamimetic selected from the group consisting of:

Bambuterol

Bitolterol

Carbuterol

Clenbuterol

Fenoterol

Hexoprenaline

Ibuterol

Pirbuterol

Procaterol

Reproterol

Salbutamol

Salmeterol

Sulphonterol

Terbutaline

Tulobuterol 1-(2-fluoro-4-hydroxyphenyl)-2-[4-(1-benzimidazolyl)-2-methyl-2-butylamino]ethanol Erythro-5'-Hydroxy-8'-(1-hydroxy-2-isopropylamino-butyl)-2H-1,4-benzoxazine-3-(4H-)one 1-(4-amino-3-chloro-5-trifluoromethylphenyl)-2-tert.-butyl-amino)ethanol, and 1-(4-ethoxycarbonylamino-3-cyano-5-fluorophenyl)-2-(tert.-butylamino)ethanol in combination with a second pharmaceutically active compound or substance which is an anti-cholinergic selected from the group consisting of Ipratropium bromide Oxitropium bromide Trospium chloride Benzilic acid N-β-fluorethylnortopine ester and Methobromide, and wherein such betamimetic compound or substance and such anti-cholinergic compound or substance together comprise from about 0.001% to about 5% by weight.

* * * * *